US011771861B2

(12) United States Patent
Boye et al.

(10) Patent No.: US 11,771,861 B2
(45) Date of Patent: Oct. 3, 2023

(54) CPAP TETHER

(71) Applicants: Branden Boye, Marinette, WI (US); Matthew Colangelo, Marinette, WI (US); William J. Suave, Sturgeon Bay, WI (US)

(72) Inventors: Branden Boye, Marinette, WI (US); Matthew Colangelo, Marinette, WI (US); William J. Suave, Sturgeon Bay, WI (US)

(*) Notice: Subject to any disclaimer, the term of this patent is extended or adjusted under 35 U.S.C. 154(b) by 1022 days.

(21) Appl. No.: 16/654,967

(22) Filed: Oct. 16, 2019

(65) Prior Publication Data
US 2020/0114108 A1 Apr. 16, 2020

Related U.S. Application Data

(60) Provisional application No. 62/746,067, filed on Oct. 16, 2018.

(51) Int. Cl.
A61M 16/06 (2006.01)
A61M 16/00 (2006.01)

(52) U.S. Cl.
CPC .... A61M 16/0666 (2013.01); A61M 16/0003 (2014.02); A61M 16/0051 (2013.01); A61M 2205/3331 (2013.01)

(58) Field of Classification Search
CPC .......... A61M 16/0003; A61M 16/0666; A61M 16/0051
See application file for complete search history.

(56) References Cited

U.S. PATENT DOCUMENTS

| 4,378,012 A * | 3/1983 | Brown | A61M 16/0497 128/DIG. 26 |
| 4,641,646 A * | 2/1987 | Schultz | A61M 16/0497 128/207.14 |
| 4,995,384 A * | 2/1991 | Keeling | A61M 16/0672 128/207.18 |
| 5,672,159 A * | 9/1997 | Warrick | A61M 16/0683 604/179 |
| 5,752,511 A | 5/1998 | Simmons et al. | |
| 5,772,258 A * | 6/1998 | Dyer | F16L 3/1203 285/252 |
| 5,782,236 A * | 7/1998 | Ess | A61M 25/02 24/339 |
| 5,934,276 A * | 8/1999 | Fabro | A61M 25/02 128/207.14 |
| 6,105,573 A | 8/2000 | Delaplane et al. | |

(Continued)

FOREIGN PATENT DOCUMENTS

| AU | 2011313825 B2 * | 7/2015 | ........ A61M 16/0057 |
| CN | 102648018 B * | 3/2016 | ............ A61M 16/06 |

(Continued)

Primary Examiner — Michael J Tsai
(74) Attorney, Agent, or Firm — Amundsen Davis, LLC

(57) ABSTRACT

An apparatus comprises a first ring and a second ring. The first ring may have a first diameter and a first cutout portion. The second ring may have a second diameter and a second cutout portion, and may further comprise a pair of protrusions extending upwardly from a surface of the ring. A tubular connector may couple the first ring and the second ring. In some embodiments, a sensor may be coupled to the tubular connector. The sensor may include an alarm and a breakaway connector.

10 Claims, 7 Drawing Sheets

(56) References Cited

U.S. PATENT DOCUMENTS

| | | | |
|---|---|---|---|
| 6,612,309 B1 | 9/2003 | Ancona | |
| 7,318,437 B2* | 1/2008 | Gunaratnam | A61M 16/0666 |
| | | | 128/207.11 |
| 7,347,454 B2 | 3/2008 | Martus | |
| 7,744,043 B2 | 6/2010 | Otinger | |
| 9,308,343 B2 | 4/2016 | Groll et al. | |
| 10,350,376 B2* | 7/2019 | White | A61M 16/0672 |
| 10,786,641 B1* | 9/2020 | Patraka | A61J 15/0061 |
| 2004/0139973 A1* | 7/2004 | Wright | A61M 16/0672 |
| | | | 128/207.18 |
| 2005/0061326 A1 | 3/2005 | Payne | |
| 2008/0185359 A1 | 8/2008 | Baxter | |
| 2009/0039210 A1 | 2/2009 | Yates et al. | |
| 2009/0078259 A1* | 3/2009 | Kooij | A61M 16/0875 |
| | | | 128/205.25 |
| 2010/0244437 A1 | 9/2010 | O'Neil et al. | |
| 2011/0146685 A1* | 6/2011 | Allan | A61M 16/06 |
| | | | 128/206.26 |
| 2011/0265796 A1* | 11/2011 | Amarasinghe | A61M 16/0633 |
| | | | 128/206.28 |
| 2012/0168571 A1 | 7/2012 | Bond et al. | |
| 2013/0098359 A1* | 4/2013 | Becker | A61M 16/0683 |
| | | | 128/201.13 |
| 2014/0090649 A1* | 4/2014 | Groll | A61M 16/06 |
| | | | 128/205.25 |
| 2015/0137505 A1* | 5/2015 | Ford | F01N 13/1838 |
| | | | 285/81 |
| 2015/0224274 A1* | 8/2015 | Siew | A61M 16/0622 |
| | | | 128/206.24 |
| 2016/0058966 A1* | 3/2016 | O'Donnell | A61M 16/0683 |
| | | | 128/205.25 |
| 2016/0089261 A1 | 3/2016 | Quinn | |
| 2016/0166822 A1* | 6/2016 | Dodson | A61M 39/10 |
| | | | 604/533 |
| 2017/0119988 A1* | 5/2017 | Allan | A61M 16/0816 |
| 2017/0151409 A1* | 6/2017 | Peacock | A61M 16/0875 |
| 2017/0203072 A1 | 7/2017 | Tonning et al. | |
| 2019/0388303 A1* | 12/2019 | Sharaiha | A61J 15/0003 |
| 2021/0187229 A1* | 6/2021 | Brar | A61M 16/0493 |

FOREIGN PATENT DOCUMENTS

| | | | | |
|---|---|---|---|---|
| CN | 105816949 A | * | 8/2016 | A61M 16/06 |
| GB | 2244924 A | * | 12/1991 | A61M 16/0488 |
| WO | WO-0216816 A1 | * | 2/2002 | F16L 35/00 |
| WO | WO-2006138151 A2 | * | 12/2006 | F16L 33/03 |
| WO | WO-2010131189 A1 | * | 11/2010 | A61M 16/06 |
| WO | WO-2014035261 A1 | * | 3/2014 | A61M 16/06 |
| WO | WO-2014142681 A1 | * | 9/2014 | A61M 16/0003 |
| WO | WO-2015193833 A2 | * | 12/2015 | A61B 17/34 |
| WO | WO-2022229909 A1 | * | 11/2022 | A61M 16/20 |

* cited by examiner

CPAP TETHER

PRIORITY CLAIM

This application claims priority to U.S. Provisional Patent Application No. 62/746,067, filed Oct. 16, 2018, the contents of which are hereby incorporated by reference.

BACKGROUND

Continuous positive airway pressure (CPAP) therapy refers to a particular type of air pressure ventilator that assists in keeping a user's airway open. A CPAP setup often includes a mask worn by a user, a hose, and a machine. One end of the hose is coupled to the machine and the other end is coupled to the mask to deliver a particular, consistent air pressure to the user.

DETAILED DESCRIPTION

Figure 1:
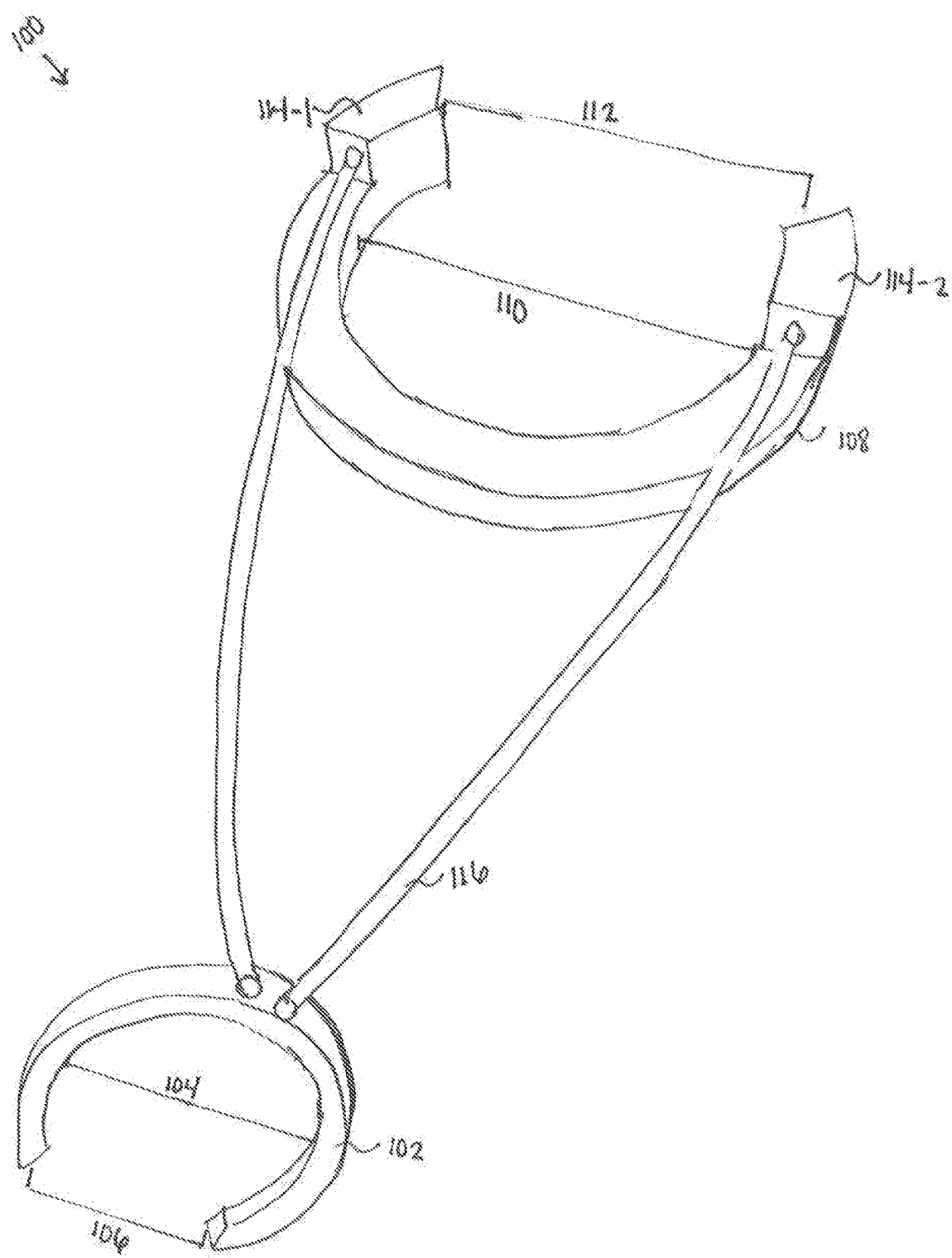
FIG. 1 is an example apparatus for a CPAP tether consistent with the present disclosure.

Continuous positive airway pressure (CPAP) therapy uses air pressure to aid in keeping the airway of a user open, particularly during sleep. A CPAP setup includes a flow generator machine (also called a CPAP machine) to provide the pressure and a mask worn by a user over the mouth and nose. A flexible hose connects the CPAP machine with the CPAP mask, allowing the user to be provided with the particular air pressure they need.

Both a CPAP mask and the hose are designed to be cleaned by a user. Therefore, a hose connects to a CPAP mask using a friction fit. This allows the hose and the mask to be disconnected with ease for cleaning and reconnected when cleaning is complete. However, because the CPAP mask and the hose are connected using only a friction fit, the hose may become disconnected from the mask during use of the CPAP setup. When this happens, the mask, and thus the user, is not receiving the positive air pressure from the CPAP machine. This can be dangerous for the user, as CPAP therapy is often used to treat conditions such as sleep apnea, where a person stops breathing during sleep.

One way to combat hose disconnection is through application of an adhesive, such as a caulk or an epoxy. A silicone caulk or epoxy, or similar, may be applied to the hose and/or mask connector to provide additional bulk and/or tackiness to the connector. As a result, the strength of the friction fit between the CPAP mask and hose may be increased. However, the adhesive may not maintain its integrity permanently; that is, with repeated use over time, the adhesive may wear and lose its tackiness, necessitating reapplication.

Another way to combat hose disconnection is through extra cleaning to rid the hose and/or mask connection points of any residue or buildup. Removal of the built-up residue may return the hose to a state more comparable to when it was new. This solution is cost effective because it requires nothing beyond soap and water; however, much like the adhesive, extra cleaning is not a permanent solution. Residue and buildup may reform on the hose and/or mask, resulting in the need for extra cleaning once again. Additionally, such extra cleaning takes time beyond the time already used to wash the hose and mask for cleaning.

Another option is to simply replace the CPAP hose when the hose currently being used has begun to disconnect from the CPAP mask. A new CPAP hose is tackier and lacks residue or stress caused by repeated use of the CPAP system. Although a CPAP hose is relatively inexpensive, continuing to replace the hose every time disconnection becomes an issue does begin to add up. In addition, the only area that is an issue may be the connection point between the CPAP hose and mask, meaning that a hose that is otherwise still able to be used is being discarded.

A CPAP tether consistent with the present disclosure, by contrast, both assists in keeping the CPAP mask and hose connected and, in the event of a disconnect, retains the hose close to the user. A first ring couples to the CPAP mask around the connection point between the mask and the hose, while a second ring couples to the hose. A tube disposed the first ring and the second ring couples the rings, and thus the CPAP mask and hose, together. The CPAP tether may be removable for cleaning, but may otherwise remain on the CPAP system, i.e., may not need installation every time the CPAP system is used.

FIG. 1 is an example apparatus 100 for a CPAP tether consistent with the present disclosure. Apparatus 100 includes a first ring 102. First ring 102 may have a first diameter 104. First diameter 104 may be sized to couple to a CPAP hose, although examples are not so limited. First ring 102 may further have a first cutout portion 106. As shown in FIG. 1, first cutout portion 106 may comprise a portion of ring 102 such that ring 102 is substantially U-shaped. First ring 102 may be made of silicone, rubber, plastic, or any similar material that is simultaneously rigid yet is able to be manipulated to fit onto and be removed from a CPAP hose.

A plurality of apertures may be disposed opposite first cutout portion 106. Although two apertures are shown in FIG. 1, examples are not so limited and other numbers of apertures may be used. The apertures may be disposed opposite the first cutout portion 106, as shown in FIG. 1; however, the apertures may be disposed at another location on the first ring 102 with respect to the first cutout portion 106. For example, an aperture may be located on each side of the first cutout portion 106 or at any other location on first ring 102.

Apparatus 100 further includes a second ring 108. Second ring 108 may have a second diameter 110. Second diameter 110 may be sized to couple to a CPAP mask. Second diameter may further have a second cutout portion 112. As shown in FIG. 1, second cutout portion 112 may comprise a portion of ring 108 such that ring 108 is substantially U-shaped, similar to first ring 102.

Second ring 108 may further include a pair of protrusions 114-1, 114-2 (collectively, protrusions 114). Protrusions 114 may extend upwardly from an upper surface of second ring 108. As shown in FIG. 1, protrusions 114 may be disposed such that they are substantially perpendicular to ring 108; however, examples are not so limited and other orientations may be present. Protrusions 114 may be integrally formed with second ring 108; that is, protrusions 114 may be formed from the same piece of material as second ring 108. Each protrusion of protrusions 114 may be disposed adjacent to one side of second cutout portion 112, such that second cutout portion 112 is bounded on each side by protrusions 114.

A pair of apertures may be disposed within second ring 108. In some examples, the apertures may be disposed within protrusions 114; that is, each protrusion 114 may include an aperture. The apertures may extend through the length of protrusions 114 or may extend only partially through. In some examples, the apertures may be disposed such that they are substantially parallel to the surface of second ring 108.

Apparatus 100 may further include a tubular connector 116. Tubular connector 116 may be used to couple the first ring 102 and the second ring 108. In some examples, first ring 102 and second ring 108 may be coupled to one another by tubular connector 116 at the plurality of apertures. For example, tubular connector 116 may be inserted into one aperture of the pair of apertures that are part of second ring 108. Tubular connector 116 may then be threaded through the plurality of apertures located on first ring 102, with the remaining free end being inserted into the second aperture of the pair of apertures of second ring 108. Of course, examples are not so limited and other configurations may be used to couple first ring 102 and second ring 108 with tubular connector 116. Tubular connector 116 may be a rubber, plastic, or similarly flexible tube, and may have a diameter that is sized to be received by the apertures.

Figure 2:
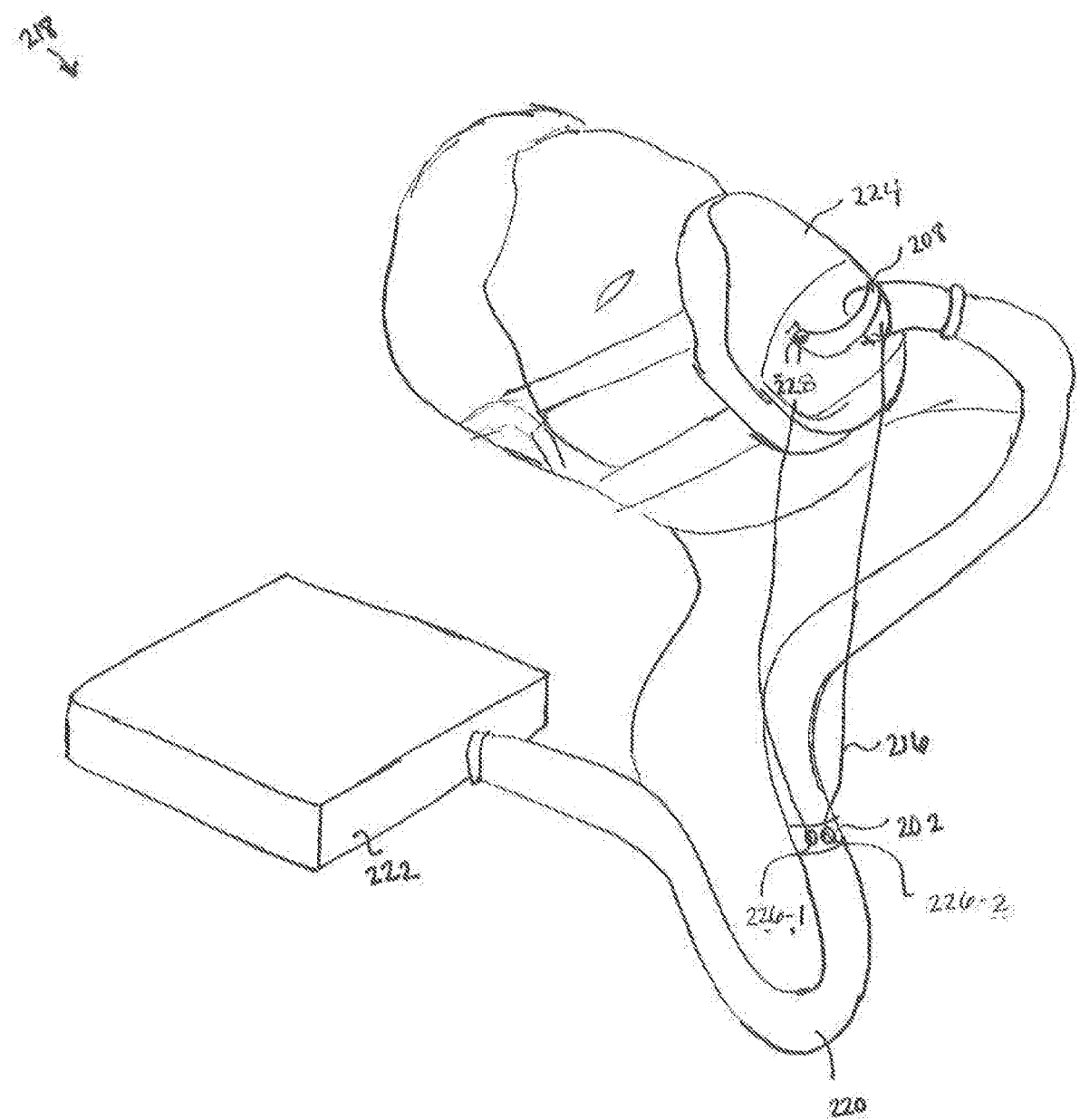
FIG. 2 is an example system for a CPAP tether consistent with the present disclosure.

FIG. 2 is an example system 218 for a CPAP tether consistent with the present disclosure. System 218 may include a CPAP hose 220 and a CPAP mask 224. One end of CPAP hose 220 may be connected to a CPAP machine 222; the other end may be coupled to the CPAP mask 224 such that the CPAP hose 220 provides air to the CPAP mask 224. The CPAP mask 224 may be fastened to the head and face of a user by straps or another securement mechanism.

System 218 may further include a first ring 202. First ring 202 may be akin to first ring 102, discussed with respect to FIG. 1. First ring 202 may comprise a substantially circular disk or ring with a first inner diameter and a first outer diameter. The first inner diameter may be akin to first diameter 104, discussed with respect to FIG. 1. The first outer diameter may be greater than the first inner diameter such that first ring 202 has a thickness. As described with respect to FIG. 1, the first inner diameter may be sized such that first ring 202 is able to couple to CPAP hose 220.

A first cutout may be disposed within a portion of the first disk of first ring 202. The first cutout may be akin to cutout 106, discussed with respect to FIG. 1. As described with respect to FIG. 1, the first cutout may be disposed such that first ring 202 is substantially U-shaped, and thus able to removably couple to the CPAP hose 220.

A plurality of apertures 226-1, 226-2 (collectively, apertures 226) may be disposed opposite the first cutout on first ring 202. Although two apertures 226 are shown in FIG. 2, examples are not so limited and other numbers of apertures may be used. Additionally, apertures 226 may be disposed at a location or locations other than, or in addition to, opposite the first cutout; for example, apertures 226 may be disposed on a side of first ring 202, although examples are not so limited. Apertures 226 may be sized to receive a tubular connector, discussed further herein.

System 218 may further include a second ring 208. Second ring 208 may be akin to second ring 108, discussed with respect to FIG. 1, and comprise a second substantially circular disk or ring. Second ring 208 may further include a second inner diameter and a second outer diameter. The second inner diameter may be akin to second diameter 110, discussed with respect to FIG. 1, and may be sized to receive a CPAP mask such as CPAP mask 224. In some examples, the second ring 208 may couple to the CPAP mask 224 at a location of a connection between the CPAP mask 224 and the CPAP hose 220, such that CPAP hose 220 is retained in its location with respect to CPAP mask 224. The second outer diameter may be greater than the second inner diameter, such that second ring 208 has a thickness.

A second cutout may be disposed within second ring 208. The second cutout may be akin to cutout 112, discussed with respect to FIG. 1, and may be sized such that second ring 208 is able to couple to CPAP mask 224. A pair of protrusions (such as protrusions 114, shown in FIG. 1) may be disposed on either side of the second cutout. The protrusions may extend upwardly from the second disk and may be substantially perpendicular thereto. In some examples, the protrusions may be integrally formed as part of the second disk. That is, the protrusions may be manufactured as part of the second disk, as opposed to being a separately attached piece.

Within the pair of protrusions may be a pair of apertures 228. Although only a single aperture 228 is shown in FIG. 2, it is to be understood that a corresponding aperture may be located opposite the aperture 228. Apertures 228 may be disposed within the pair of protrusions such that apertures 228 are substantially parallel to the surface of second ring 208. Further, apertures 228 may be sized to receive a tubular connector, discussed further herein.

System 218 may include a tubular connector 216. Tubular connector 216 may be akin to tubular connector 116, discussed with respect to FIG. 1, and may couple the first ring 202 to the second ring 208. In some examples, the tubular connector 216 may couple the first ring 202 to the second ring 208 at apertures 226 and 228. For example, a first end of tubular connector 216 may couple with a first aperture of the pair of apertures 228 on the second ring 208. The first end of tubular connector 216 may have a knot or stop to prevent being pulled through aperture 228. A middle portion of the tubular connector 216 may couple with the plurality of apertures 226 on the first ring 226. In some examples, the tubular connector 216 may be threaded through the plurality of apertures 226 such that a loop is formed between the tubular connector 216 and the apertures 226. A second end of the tubular connector 216 may then be coupled to the second aperture of the pair of apertures 228 of the second ring. As with the first end, the second end of tubular connector 216 may have a knot or stop to prevent being pulled through the second aperture 228. The first ring 202 may thus be coupled to the second ring 208. Of course, other methods of connection using the tubular connector 216 may be used, and the method provided is not so limited.

Figure 3:
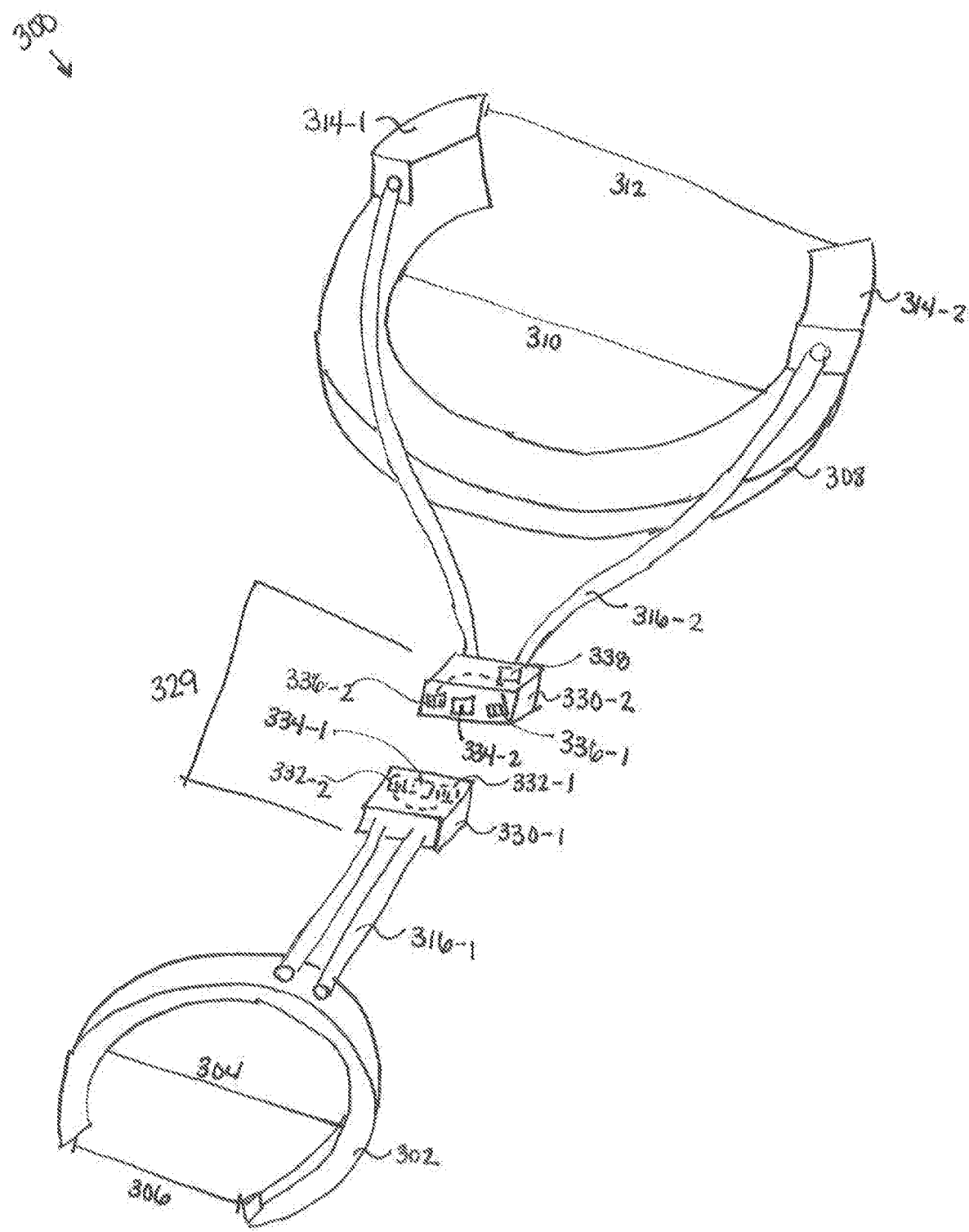
FIG. 3 is another example apparatus for a CPAP tether consistent with the present disclosure.

FIG. 3 is another example apparatus 300 for a CPAP tether consistent with the present disclosure. Apparatus 300 may include a first ring 302; first ring 302 may be akin to first ring 102 and first ring 202, discussed with respect to FIGS. 1 and 2, respectively. The first ring 302 may have a first diameter 304 and a first cutout portion 306. First diameter 304 may be akin to first diameter 104 and first cutout portion 306 may be akin to first cutout portion 106, discussed with respect to FIG. 1.

Apparatus 300 may further include a second ring 308. Second ring 308 may be akin to second ring 108 and second ring 208, discussed with respect to FIGS. 1 and 2, respectively. Second ring 308 may have a second diameter 310 and a second cutout portion 312; second diameter 310 may be akin to second diameter 110 and second cutout portion 312 may be akin to second cutout portion 112, discussed with respect to FIG. 1. Second ring 308 may further comprise a pair of protrusions 314-1, 314-2 (collectively, protrusions 314) extending upwardly from a surface of second ring 308. Protrusions 314 may be akin to protrusions 114, discussed with respect to FIG. 1.

Apparatus 300 may include a sensor 329. As used herein, a sensor refers to a device that detects a physical stimulus or event and records, indicates, or otherwise responds to it. Sensor 329 may include a first sensor portion 330-1 and a second sensor portion 330-2. A first plurality of circuits 332-1, 332-2 (collectively, circuits 332) may be disposed within first sensor portion 330-1. Although two circuits 332 are shown, examples are not so limited, and other numbers of circuits may be used. Circuits 332 may include resistors, capacitors, transistors, and other similar electrical and electromagnetic components.

A second plurality of circuits 336-1, 336-2 (collectively, circuits 336) may be disposed within second sensor portion 330-2. Although two circuits 336 are shown, other numbers of circuits may be used. However, the number of circuits 336 disposed within second sensor portion 330-2 is to be identical to the number of circuits 332 disposed within first sensor portion 330-1 to allow for proper coupling of the sensor 329 (described further herein). As with circuits 332, circuits 336 may include resistors, capacitors, transistors, and other similar electrical and electromagnetic components.

A plurality of connectors 334-1, 334-2 (collectively, connectors 334) may be disposed within the first portion of the sensor 330-1 and the second portion of the sensor 330-2. As shown in FIG. 3, each sensor portion 330-1, 330-2 may include a portion of connectors 334. Connectors 334 may join the first portion of the sensor 330-1 to the second portion of the sensor 330-2. Connectors 334 may be magnetic connectors, clip connectors, or any other type of breakaway connections.

When connectors 334 are joined, thus joining first portion of the sensor 330-1 and second portion of the sensor 330-2, the first plurality of circuits 332 may couple with the second plurality of circuits 336. When coupled, first plurality of circuits 332 and second plurality of circuits 336 may form a complete circuit, that is, a circuit through which electricity is able to flow. By contrast, when the connectors 334 are disengaged, the first plurality of circuits 332 may disconnect from the second plurality of circuits 336. This may create a break in the complete circuit.

An alarm may be disposed within sensor 329. As used herein, an alarm refers to a device that makes a sound or uses another indicator, such as a light, to alert a user to something. In the case of sensor 329, the alarm may be used to alert a user of system 300 that the system 300 has moved, slipped, or shifted. For example, the alarm may alert a user that the first ring 302 has moved down on the CPAP hose. The alarm may be coupled to circuits 332 and/or circuits 334, either physically or wirelessly. In some examples, the alarm may be located on a CPAP machine, such as CPAP machine 222 (discussed with respect to FIG. 2). In such examples, sensor 329 may be wirelessly coupled to the alarm.

The alarm may emit an alert, such as a noise or a flashing light, when the first plurality of circuits 332 is disconnected from the second plurality of circuits 336. Said differently, the alarm may activate when the complete circuit created by the first plurality of circuits 332 and the second plurality of circuits 336 is broken or opened. In such examples, the alarm may alert a user of the apparatus 300 that the sensor 329 has disconnected into its constituent portions 330-1, 330-2. This may correspond to, for example, the first ring 302 moving down with respect to the CPAP hose, the second ring 308 moving with respect to the CPAP mask, or a combination thereof.

In some examples, sensor 329 may include a transmitter operable over, for example, IEEE 802.15.15 (Bluetooth®) or over IEEE 802.11 (Wi-Fi) to transmit a notice that the alarm is engaged, that the alarm is active (i.e., emitting an alert), or any other notification relative to the alarm and sensor 329. In some examples, the notice may be transmitted to a portable electronic device, such as a smartphone or a tablet. The portable electronic device may include an application to wirelessly couple to the sensor 329, and more particularly to the transmitter contained within the sensor 329, to allow receipt of such notices. For instance, an application may allow a user to be alerted on their portable electronic device when the alarm is activated.

In some examples, the alarm may be armed when the first plurality of circuits 332 is coupled with the second plurality of circuits 336 through coupling of the sensor portions 330-1, 330-2 by connectors 334. As used herein, arming the alarm refers to the alarm being primed and prepared to activate if a triggering event occurs. With respect to apparatus 300, the triggering event may correspond to a disconnection of connectors 334, causing a separation of first sensor portion 330-1 and second sensor portion 330-2. As described previously, disconnection of the first sensor portion 330-1 and the second sensor portion 330-2 may cause a break in a circuit comprised of circuits 332, 336. When the first plurality of circuits 332 is disconnected from the second plurality of circuits 336, the alarm may emit an alert, such as a noise, a flashing light, or a similar alert. The alert may continue for a predetermined amount of time (e.g., thirty seconds) or may continue until a user re-arms the alarm by connecting first sensor portion 330-1 and second sensor portion 330-2, thus re-completing the circuit formed by circuits 332, 336. In either case, the alert by the alarm may serve to let a user know that the apparatus has moved, shifted, or otherwise been disturbed and should be adjusted.

Figure 4:
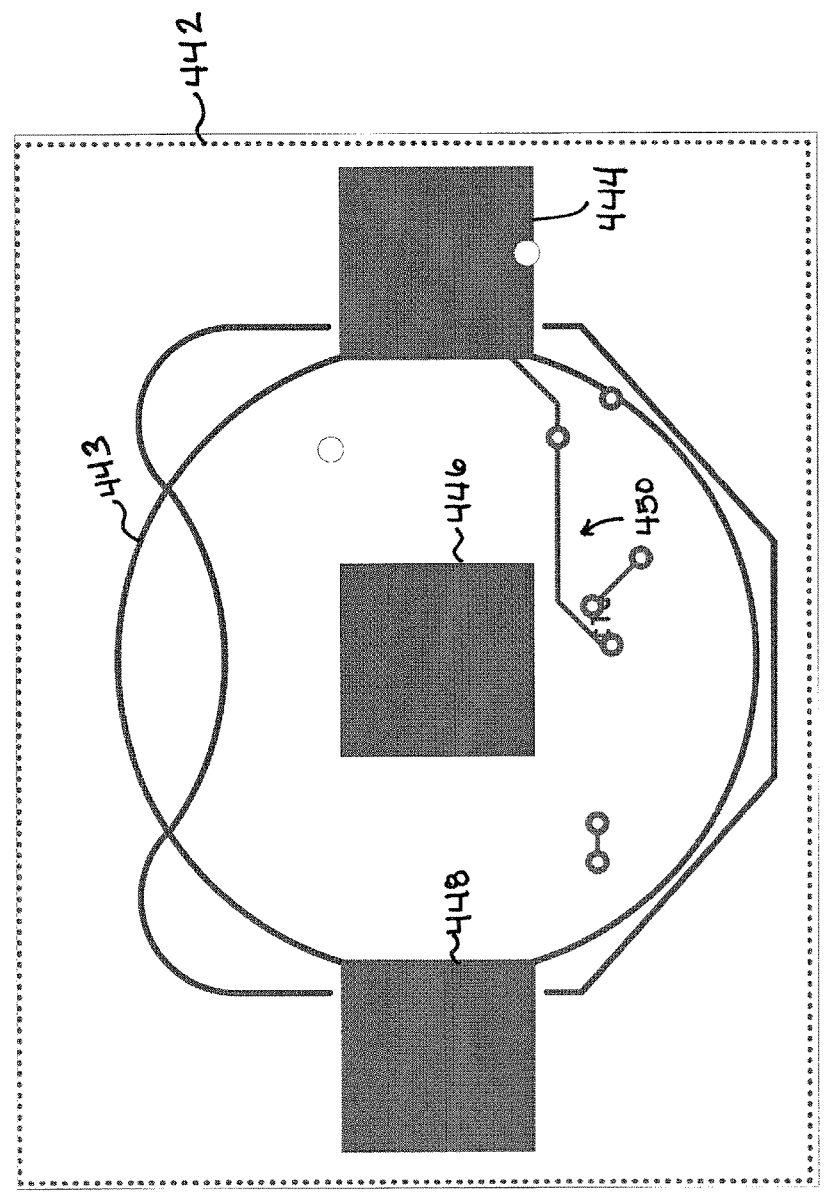
FIG. 4 is a bottom view of an alarm system circuit board for use with a CPAP tether consistent with the present disclosure.

FIG. 4 is a bottom view of an alarm system circuit board 440 for use with a CPAP tether consistent with the present disclosure. Circuit board 440 may be disposed within the CPAP tether itself in, for example, a sensor, such as sensor 329, discussed with respect to FIG. 3, and may correspond to first plurality of circuits 332 and/or second plurality of circuits 336. Circuit board 440 includes a base 442. Base 442 may be a regular printed circuit board (PCB), having a base, often made of fiberglass, a conductive layer, often made of copper, and a soldermask disposed atop the conductive layer. Base 442 may also be a flexible PCB. In such examples, base 442 may be manufactured of a flexible material, such as rubber, plastic, or any other suitable material. A flexible PCB may further include a layer of conductive material, such as copper, and a layer of dielectric material, such polyimide. When base 442 is a flexible PCB, the circuit board 440 is able to be deformed, bent, or otherwise manipulated within integration of the circuit board 440 into the CPAP tether.

Base 442 may include a printed circuit element 443. As used herein, a printed circuit element refers to a portion of a circuit included on a circuit board, such as is included on base 442, that is shown and used as a reference point for building of a circuit with additional elements. Printed circuit element 443 may be printed directly on base 442, and may be printed with conductive material, such that additional components can be directly added to printed circuit element 442, or may be printed with non-conductive material, such that printed circuit element 443 serves more as a visual guide for placement of additional components.

Additional placement guides 444, 446, and 448 may be included on base 442. Although three placement guides are shown in FIG. 4, examples are not so limited, and more or fewer placement guides may be included. As with printed circuit element 443, placement guides 444, 446, and 448 may be printed with conductive material, allowing direct integration of additional elements onto the placement guides 444, 446, and 448, or may be printed with non-conductive material to serve as a visual guide. In some examples, placement guide 444 may correspond to a battery placement, placement guide 446 may correspond to a snooze button placement, and placement guide 448 may correspond to a connector placement. These elements are discussed further herein with respect to FIGS. 5 and 7.

Base 442 may further include wiring connections 450. Wiring connections 450 may be disposed between placement guide 444 (which may correspond to a battery) and additional sections of base 442, such that the element corresponding to placement guide 444 may be wired to or connected with additional elements disposed on base 442. The wiring connections 450 are discussed further herein with respect to FIGS. 5-7.

Figure 5:
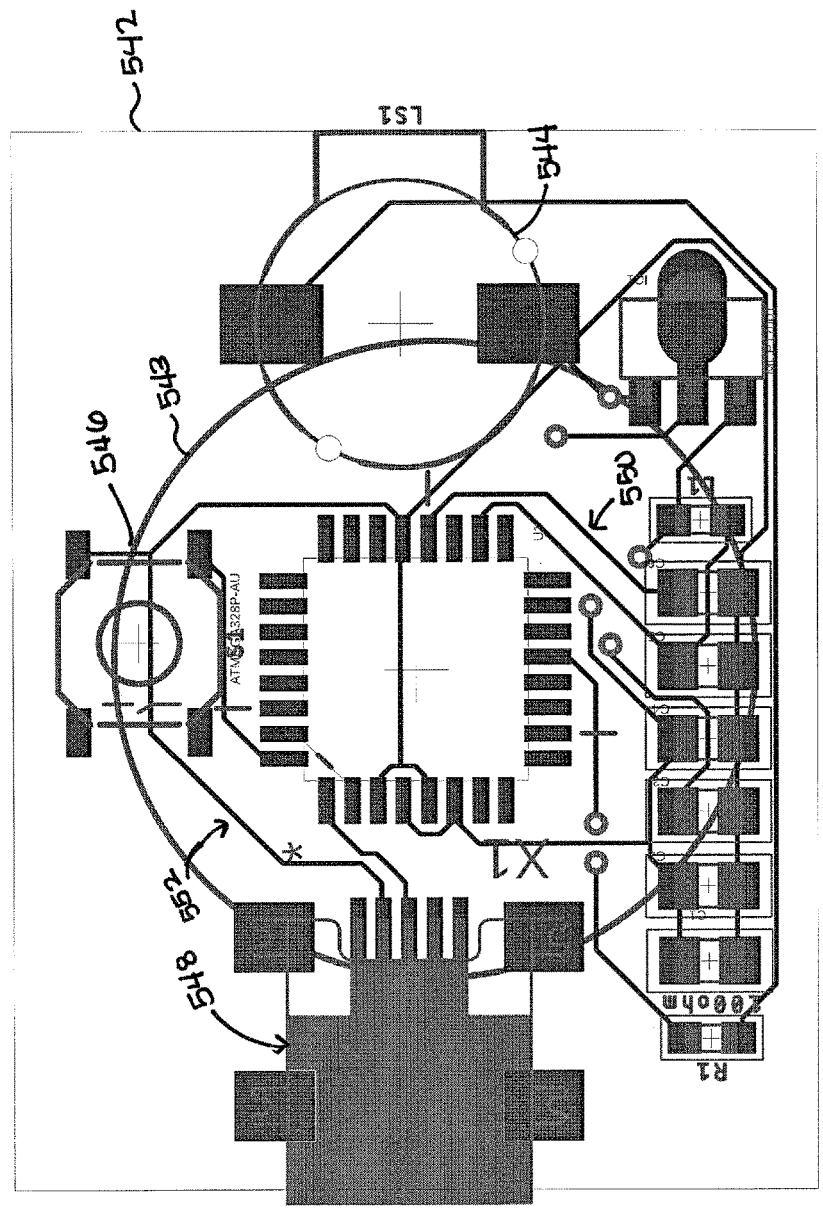
FIG. 5 is another view of the alarm system circuit board of FIG. 4 for use with a CPAP tether consistent with the present disclosure.

FIG. 5 is another view of the alarm system circuit board 540 of FIG. 4 for use with a CPAP tether consistent with the present disclosure. As can be seen in FIG. 5, circuit board 540 shows additional elements that would be placed atop the circuit board of FIG. 4. Circuit board 540 includes a base 542, which may be akin to base 442 discussed with respect to FIG. 4, and which may have a printed circuit element 543 disposed thereon (printed circuit element 543 is akin to printed circuit element 443, also discussed with respect to FIG. 4).

Circuit board 540 may further include a battery 544. Battery 544 may be placed in accordance with the location placement guide 444, shown in FIG. 4. Battery 544 may be a lithium-ion battery, an alkaline battery, or any other suitable type of battery. In some examples, battery 544 may be a watch battery, a hearing aid battery, or another type of small battery, such that battery 544 may fit within the circuit board 540 and, further, within the larger CPAP tether system (e.g., within sensor 329, discussed with respect to FIG. 3).

A snooze button 546 may be included as part of circuit board 540. As used herein, a snooze button refers to a button or switch that, when activated, may be used to temporarily stop an alarm or other type of notification. Snooze button 546 may be a capacitative or other push button, a switch, or any other type of selectively activated device. As shown in FIG. 5, snooze button 546 may be placed at the location of placement guide 446, shown in FIG. 4, and may be connected via a wired connection to battery 544. As a result, snooze button 546 may be powered by battery 544. That is, when activated, snooze button 546 may draw power from battery 544. In such examples, activating snooze button 546 by, for example, depressing a push-button, may complete or disrupt a circuit, depending on the setup of circuit board 540, for a selected period of time. For example, snooze button 546 may be depressed upon activation of an alarm, such as the alarm discussed with respect to FIG. 3. As discussed with respect to FIG. 3, the alarm may be activated when the individual portions sensor 329 becomes disconnected from one another, resulting in, e.g., an audible alarm, a visual alarm, a vibration, or a combination thereof. Activating snooze button 546 may temporarily stop the alarm from alerting, allowing a user to reconnect the sensor portions. The snooze button 546 may only stop the alarm for a period of time (e.g., one minute) after which the alarm may begin alerting again. This allows a user to reconnect the sensor and adjust the CPAP mask and CPAP tether without the additional distraction of an alarm. In such examples, upon reconnection of the sensor 329, snooze button 546 may be returned to its non-activated position (e.g., a non-depressed push button or a switch in the 'off' position). As shown in FIG. 5, snooze button 546 may also be connected to a connector 548, discussed further herein, such that snooze button 546 is integrated with each of the other components of circuit board 540.

Circuit board 540 may further include a connector 548. Connector 548 may be akin to connectors 334, discussed with respect to FIG. 3, and, as shown in FIG. 5, may be placed in accordance with the location of placement guide 448 shown in FIG. 4. As discussed with respect to FIG. 3, connector 548 may be a magnetic connector, a mechanical connector (e.g., a clip), a micro USB or USB connector, a thunderbolt connector, or any other type of connector that is able to selectively breakaway in response to a particular amount of force or pressure. As shown in FIG. 5, connector 548 may be wired to snooze button 546 and/or to battery 544. In some examples, connector 548 may include an alarm that, when connector 548 is disconnected, provides an alert, such as a visual alert, audio alert, or tactile alert. In such examples, battery 544 may provide power to the alarm, such that when connector 548 is disconnected, a circuit of circuit board 540 is completed and the alarm activates. As discussed previously, snooze button 546 may be used to temporarily disrupt the circuit between connector 548 and battery 544 to allow a user to reconnect connector 548 with another portion of the CPAP tether. The other portion may be, for example, a mating physical connector or a magnetic connector, although examples are not so limited.

A first set of wiring connections 550 may be disposed on circuit board 540, and may be akin to wiring connections 450, discussed with respect to FIG. 4. As can be seen in FIG. 5, the first set of wiring connections 550 may be used to connect battery 544 to other components, such as snooze button 546 and/or connector 548. A second set of wiring connections 552 may also be disposed on circuit board 540, and may connect connector 548 to snooze button 546. The particular setup of the wiring connections 550 and 552 are discussed further herein with respect to FIG. 6.

Figure 6:
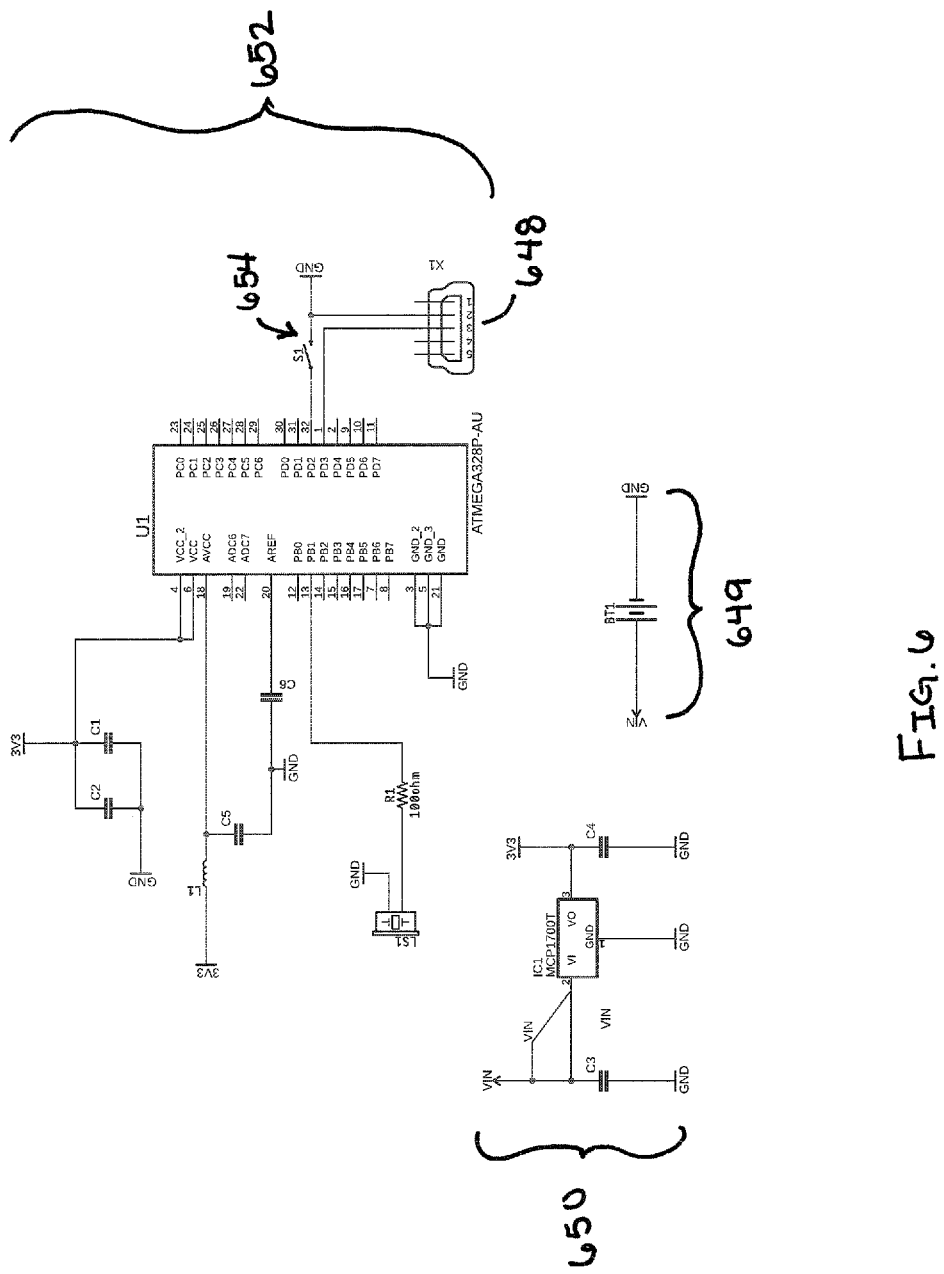
FIG. 6 is a circuit diagram of the circuits shown in FIG. 5 for use with a CPAP tether consistent with the present disclosure.

FIG. 6 is a diagram of the circuits 650, 652 shown in FIG. 5 for use with a CPAP tether consistent with the present disclosure. In addition, circuit 649, depicting a battery disposed between a ground and a Voltage In ($V_{in}$) is shown.

Circuit 650 corresponds to wiring connections 450 and 550, discussed with respect to FIGS. 4 and 5, respectively. As shown in circuit 650, an integrated circuit is disposed between two capacitors, with each element going to a ground. The $V_{in}$ of circuit 650 may correspond to the $V_{in}$ of circuit 649.

Circuit 652 corresponds to wiring connection 552, discussed with respect to FIG. 5. As shown in FIG. 6, circuit 652 includes a plurality of components, including capacitors, resistors, and inductors. It is important to note that the particular layout of circuit 652 shown is not meant to be limiting, and that some components may be added and others removed or relocated.

Circuit 652 includes a connector 648, which may be akin to connector 448 and 548, discussed with respect to FIGS. 4 and 5, respectively. Although connector 648 is depicted as a micro USB in FIG. 6, examples are not so limited, and any type of suitable connector may be used. Connector 648 may be connected to a switch 654. As used herein, a switch refers to a device or component that is used to selectively disrupt the flow of current in a circuit. When the switch is open, or "off", the circuit is incomplete, and current cannot flow. By contrast, when the switch is closed, or "on", the circuit is complete, and current is able to flow. Switch 654 may be coupled to connector 648 such that when connector 648 is coupled to its mate, the circuit is complete and the switch is closed. If connector 648 becomes disconnected, or uncoupled, from its mate, the switch may be opened and the circuit broken. This disruption of the circuit by disconnection of the connector 648 may in turn trigger an alarm, as discussed with respect to FIG. 3.

Figure 7:
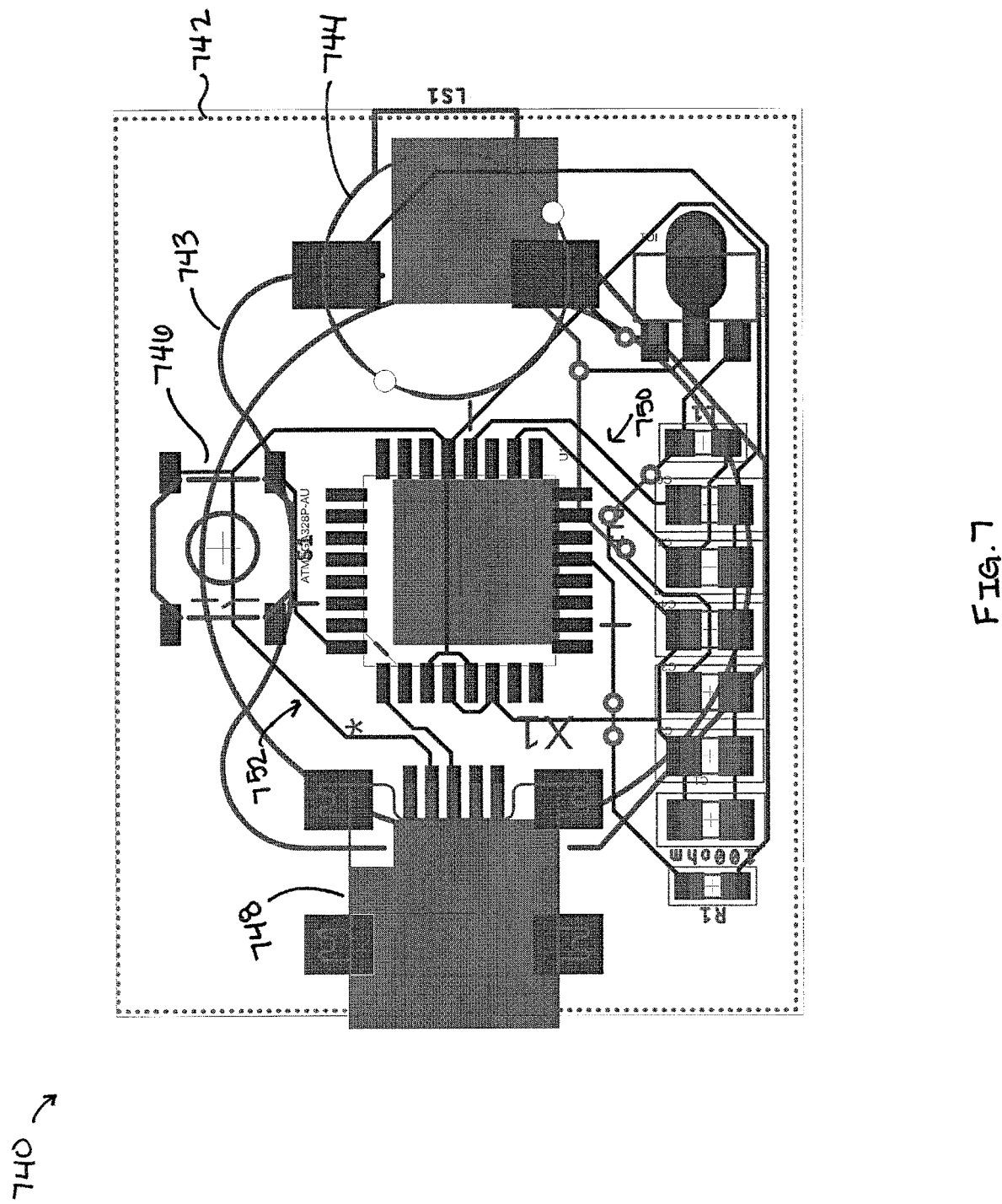
FIG. 7 is another view of the alarm system circuit board of FIG. 5 for use with a CPAP tether consistent with the present disclosure.

FIG. 7 is another view of the alarm system circuit board 740 of FIG. 5 for use with a CPAP tether consistent with the present disclosure. As with the circuit board of FIG. 5, circuit board 740 includes a base 742 onto which a printed circuit element 743 may be disposed. Circuit board 740 may further include a batter 744, a snooze button 746, and/or a connector 748. In addition, circuit board 740 may include a first set of wiring connections 750, disposed between the battery 740, connector 748, and/or snooze button 746, and a second set of wiring connections 752, disposed between the connector 748 and the snooze button 746.

In the foregoing detailed description of the present disclosure, reference is made to the accompanying drawings that form a part hereof, and in which are shown by way of illustration how examples of the disclosure may be practiced. These examples are described in sufficient detail to enable those of ordinary skill in the art to practice the examples of this disclosure, and it is to be understood that other examples may be utilized and that process and/or structural changes may be made without departing from the scope of the present disclosure.

The figures herein follow a numbering convention in which the first digit corresponds to the drawing figure number and the remaining digits identify an element or component in the drawing. Elements shown in the various figures herein can be added, exchanged, and/or eliminated so as to provide a number of additional examples of the present disclosure. In addition, the proportion and relative scale of the elements provided in the figures are intended to illustrate the examples of the present disclosure and should not be taken in a limiting sense.

The invention claimed is:

1. An apparatus, comprising:
   a first ring, wherein:
   the first ring has a first diameter; and
   the first ring has a first cutout portion;
   a second ring, wherein:
   the second has a second diameter;
   the second ring has a second cutout portion; and
   the second ring further comprises a pair of protrusions extending upwardly from a surface of the ring;
   a sensor, the sensor further comprising:
   a printed circuit board;
   a first circuit disposed on the printed circuit board;
   a second circuit disposed on the printed circuit board;
   a snooze button;
   a battery; and
   a connector, wherein the connector further comprises:
   a first connecting portion; and
   a second connecting portion, wherein the first connecting portion and the second connecting portion engage with one another; and
   an alarm; and
   a tubular connector, wherein:
   a first portion of the tubular connector couples the first portion of the sensor to the first ring; and
   a second portion of the tubular connector couples the second portion of the sensor to the second ring.

2. The apparatus of claim 1, wherein:
   the first circuit includes a switch coupled to the connector; and
   the switch is in an on position when the first connecting portion of the connector and the second connecting portion of the connector are engaged.

3. The apparatus of claim 1, wherein the switch is in an off position when the first connecting portion of the connector and the second connecting portion of the connector disengage.

4. The apparatus of claim 3, wherein the alarm emits an alert when the switch is in an off position.

5. The apparatus of claim 1, wherein:
   the snooze button is coupled to the alarm; and
   the snooze button turns off the alarm for a period of time when activated.

6. An apparatus for use with a continuous positive airway pressure (CPAP) mask having an outer diameter and a CPAP hose that provides air to the CPAP mask, the CPAP hose having an inner diameter and an outer diameter, the apparatus comprising:
   a first ring, wherein:
   the first ring has an inner diameter; and
   the first ring has a cutout portion;
   wherein the inner diameter of the first ring allows the first ring to engage the outer diameter of the CPAP hose;
   a second ring, wherein:
   the second ring has an outer diameter that allows the inner diameter of the CPAP mask to engage the outer diameter of the second ring; and
   the second ring further comprises at least one protrusion extending upwardly from a surface of the ring;
   a sensor, the sensor further comprising:
   a printed circuit board;
   a first circuit disposed on the printed circuit board;
   a second circuit disposed on the printed circuit board;
   a snooze button;
   a battery; and
   a connector, wherein the connector further comprises:
   a first connecting portion; and a second connecting portion, wherein the first connecting portion and the second connecting portion engage with one another; and
   an alarm.

7. The apparatus of claim 6, wherein:
   the first circuit includes a switch coupled to the connector; and
   the switch is in an on position when the first connecting portion of the connector and the second connecting portion of the connector are engaged.

8. The apparatus of claim 6, wherein the switch is in an off position when the first connecting portion of the connector and the second connecting portion of the connector disengage.

9. The apparatus of claim 8, wherein the alarm emits an alert when the switch is in an off position.

10. The apparatus of claim 6, wherein:
 the snooze button is coupled to the alarm; and
 the snooze button turns off the alarm for a period of time when activated.

\* \* \* \* \*